US00PP24472P2

(12) United States Plant Patent
Hurd

(10) Patent No.: US PP24,472 P2
(45) Date of Patent: May 20, 2014

(54) ***NEPETA* PLANT NAMED 'CAT'S MEOW'**

(50) Latin Name: *Nepeta faassenii*
Varietal Denomination: Cat's Meow

(71) Applicant: Kevin A. Hurd, Chicago, IL (US)

(72) Inventor: Kevin A. Hurd, Chicago, IL (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 13/815,858

(22) Filed: Mar. 16, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP23,180 P3 * 11/2012 Korlipara ..... Plt./263.1

OTHER PUBLICATIONS

Walters Gardens (retrieved from the internet at <http://www.waltersgardens.com/plants/view/?plant=2332> on Aug. 26, 2013, 1 page.*

Martin, Susan M., Walters Gardens, Inc. Wholesale Catalog, Jun. 20, 2013, Summer 2013-Spring 2014, front cover, Walters Gardens, Inc., Zeeland, Michigan, USA.

Martin, Susan M., Walters Gardens, Inc. Wholesale Catalog, Jun. 20, 2013, Summer 2013-Spring 2014, p. 158, Walters Gardens, Inc., Zeeland, Michigan, USA.

Kevin A. Hurd, Plant Breeders' Rights Application Form, Dec. 14, 2012, pp. 1-4, Canadian Food Inspection Agency.

Canadian Plant Breeders' Rights Application # 12-7812, Nepeta 'Cat;s Meow', http://www.inspection.gc.ca/english/plaveg/pbrpov/cropreport/cat/app00009033e.shtml, Nov. 21, 2013.

* cited by examiner

*Primary Examiner* — Anne Grunberg
*Assistant Examiner* — Keith Robinson

(57) ABSTRACT

The new and distinct hardy perennial Catmint plant, *Nepeta* 'Cat's Meow' has a low growing, short and compact habit with upright and slightly decumbent stems. The foliage is intermediate is size and serrate. The flowers are sky-blue with persistent smoky-purple calyces.

1 Drawing Sheet

Botanical classification: *Nepeta faassenii.*
Varietal denomination: 'Cat's Meow'.

BACKGROUND OF THE INVENTION

The new variety of Catmint, *Nepeta* 'Cat's Meow', was selected by Kevin A. Hurd from seed collected on Jul. 28, 2009 from *Nepeta faassenii* 'Walker's Low' (not patented). The pollen parent is unknown. The plant was originally given the breeder code of K9-07-02 and first evaluated in the summer of 2010, approved in final evaluation in the summer of 2011 and slated for later introduction. The new plant was selected based on the larger flowers, long blooming and compact traits. The new plant has been asexually propagated at a wholesale nursery in Zeeland, Mich. by tip cuttings with the resultant plants remaining identical to the original plant, stable and true to type in successive generations.

SUMMARY OF THE INVENTION

*Nepeta* 'Cat's Meow' is different from its parents and all other Cat Mint known to the inventor. In comparison to the female parent 'Walker's Low' the new plant is considerably shorter and more compact. The nearest comparison variety is *Nepeta* 'Novanepjun' U.S. Plant Pat. No. 23,074. 'Cat's Meow' is taller and more sprawling in habit than 'Novanepjun'. The new plant is taller, less decumbent and more upright than *Nepeta* 'Psfike' U.S. Plant Pat. No. 18,904 and is shorter than 'Junior Walker' (not patented), 'Blue Dragon' U.S. Plant Pat. No. 22,334 and 'Six Hills Giant' (not patented) and 'Purple Haze' U.S. Plant Pat. No. 23,180. In comparison to 'Purrsian Blue' (co-pending application), the new plant 'Cat's Meow' is slightly taller, slightly more spreading in habit with serrate leaf margins on larger leaves and sky-blue flowers compared to the serrate leaves with rounded teeth margins and periwinkle blue flowers. The present invention has not been evaluated under all possible environmental conditions. The phenotype may vary with changes in the environment such as light, temperature, water and nutrient availability, etc. without a change in the genotype of the plant. *Nepeta* 'Cat's Meow' is unique from all other Catmint known to the inventor in the following combined traits:

1. The habit is low growing, short and compact upright and slightly decumbent stems.
2. Foliage is moderate-sized and serrate.
3. Flowers are sky-blue with persistent smoky-purple calyces.

BRIEF DESCRIPTION OF THE DRAWINGS

The photographs of the new plant *Nepeta* 'Cat's Meow' are of a two-year old plant in a full sun display garden in Zeeland, Mich. and demonstrate the special unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
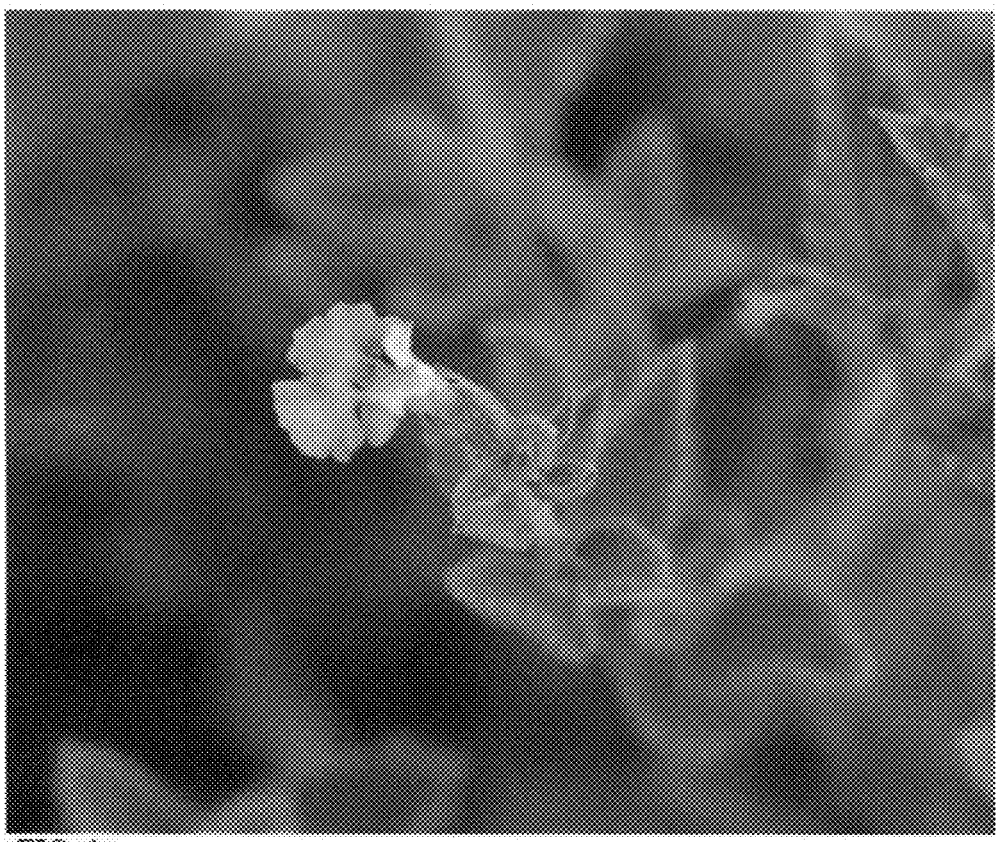
FIG. 1 shows a close-up of the flower.
Figure 2:
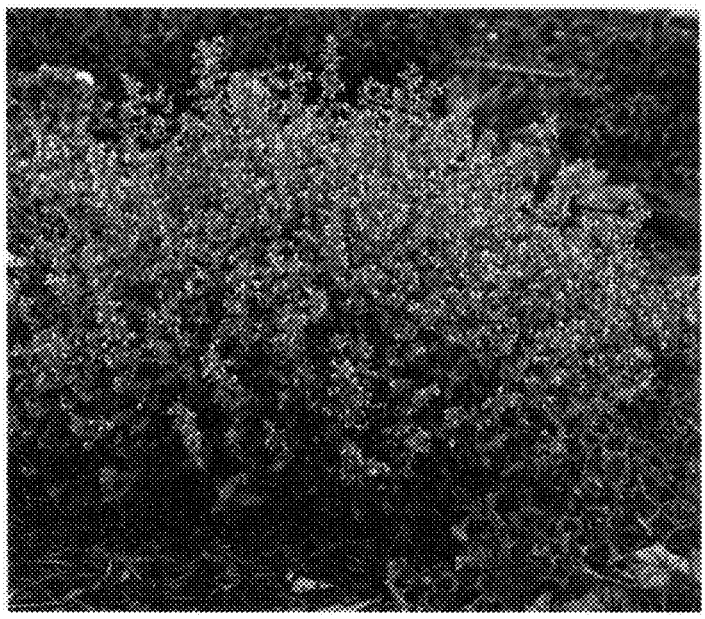
FIG. 2 shows the overall habit of *Nepeta* 'Cat's Meow'.

The following descriptions are based on a two-year old plant of *Nepeta* 'Cat's Meow' grown in a full-sun display garden in sandy loam with supplemental water and fertilizer as needed. The color references are based on the 2001 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: 'Walker's Low' (female, seed); male (pollen) parent unknown.

Plant habit: Herbaceous perennial; upright mound with side stems becoming decumbent, to about 45 cm tall and 65 cm wide at the base in flower.

Growth: Rapid; finishing in a standard #1-15 cm container in about 12 to 15 weeks from rooted plug; time to initiate roots at 23° C. about one week.

Root: Fine, freely branching; color nearest RHS 158D depending on soil type and nutrient content.

Foliage: Opposite, simple, ovate; rugose on abaxial and adaxial surfaces; margins serrate; pubescent on abaxial and adaxial surfaces; apex acute; base rounded; blade size about 18.0 mm long and 9.0 mm wide.

Venation: Longitudinal; impressed on adaxial surface and ribbed on abaxial surface.

Vein color: Darker than RHS 139A on adaxial surface and between RHS 138B and RBS 138C on abaxial surface.

Leaf color: Adaxial surface nearest RHS 139A, abaxial surface between RHS N138C and RHS 137A; distal leaves in heavy sun may develop thin line of tinting of between RHS N187A and RHS N186C along a 0.5 mm edge.

Petiole: Pubescent adaxial and abaxial; slightly flattened top to bottom; about 3.5 mm long and 2.0 mm diameter in basal region of stem becoming sessile in distal region.

Petiole color: Abaxial center nearest RHS 138C and margins between RHS 137C and RHS N138C; adaxial center between RHS 145A and RHS 145B and margins between RHS 137C and RHS N138C.

Stem: Pubescent, quadangular, about 7.0 mm across at base and 3.0 mm at just below lowest flowers; internodes average about 3.2 cm apart with greatest distance in the middle of the stem; about 14 nodes per stem.

Stem color: Between RHS N138B and RHS N138A; node color normally same as surrounding stem.

Inflorescence: Cymosely clustered with many flowers either sessile or branched at verticillasters in the upper nodes; about 10 to 35 flowers per node and about 140 per inflorescence stem or peduncle.

Peduncle: Main stem mostly vertical to about 45 cm tall with flowers on the distal 20 cm.

Pedicel: Sessile.

Flower bud: Curved clavate; about 8.0 mm long and 4.0 mm wide at the widest point one day prior to opening; adaxial surface pubescent.

Flower bud color: Petal portion between RHS 92A and RHS 92B, calyx portion nearest RHS N138A with tinting of between RHS N77A and RHS 77B.

Flowers: Zygomophic, bilabiate, synsepalous, sympetalous with basal 8.0 to 9.0 mm fused; bisexual or lacking androecium.

*Upper lip*.—Pubescent on abaxial surface, glabrous on adaxial surface; with three lobes, dorsally flattened perpendicularly to flower axis, about 12.0 mm long, vertical top lobe rounded with emarginated apex, top lobe about 6.0 mm across at widest portion; two horizontal side lobes flaring at about 90 degrees from top lobe, horizontal side lobes are rounded with rounded apices, side lobes about 1.2 mm across and long; adaxial color between RHS 91C and RHS 92C; abaxial color between RHS 91B and RHS 92C.

*Lower lip*.—Consisting of two fused lobes, dorsally flattened to perpendicular to flower axis; apex crenate with five rounded teeth, base fused; adaxial color between RHS 91B and RHS 91C with dark spots less than 0.5 mm diameter and less in tube throat nearest RHS 95A; abaxial color between RHS 93C and RHS 93B toward distal region and nearest RHS 91B in basal region.

*Calyx*.—Synsepalous, 5-merous fused into sepal tube in basal 7.0 mm and separated in distal 1.5 mm; sharply acute apex, base fused; inconspicuously veined at base and more obvious in distal region; pubescent adaxial, glabrous abaxial; persistent.

*Calyx color*.—Abaxial in high direct light distally nearest RHS 185D with darker ribs of RHS 79C and proximally or in less light nearest RHS 148D; adaxial color lighter than RHS N146D at base and tinting of nearest RHS N186C increasing with more direct sun.

*Gynoecium*.—Single compound ovary with two carpels, single gynobasic style, and stigma split in two parts; style about 9.0 mm long and 1.0 mm diameter, Style color nearest RHS N89D; Stigma split in last 2.0 mm to sharply acute apex, stigma color nearest RHS 83B.

*Ovary*.—Four-lobed, each lobe ovoid, about 1.0 mm long and 0.5 mm across, ovary color between RHS 145A and RHS N144D.

*Androecium*.—Anthers, filaments and pollen not observed under some conditions or four stamens that are adnate to the inner corolla tube.

*Anthers*.—Typically minimally developed when present, ovoid, about 1.0 mm long and 0.5 mm diameter; no pollen observed; anther color nearest RHS 146A; Filaments when present about 1.0 mm long and less than 0.5 mm diameter, filament color whiter than RHS 155D.

Flowering period: June into October in West Michigan; individual flowers remain open for up to three days.

Fragrance: Foliage and stem herbal almost minty fragrance; no fragrance detected given off by flowers.

Fruit and seed: Have not yet been observed under present conditions.

Pest and disease susceptibility: None beyond that which is typical for *Nepeta*, but typically not prone to browsing by deer or rodents.

I claim:

1. The new and distinct hardy perennial Catmint plant, *Nepeta* 'Cat's Meow' essentially as herein described and photographed useful for landscaping as a specimen, en masse, or in a container to bring color and fragrance to a garden and attract butterflies and hummingbirds.

* * * * *